United States Patent [19]
Mertens et al.

[11] Patent Number: 5,976,107
[45] Date of Patent: Nov. 2, 1999

[54] CATHETER HAVING EXTENDABLE GUIDE WIRE LUMEN

[75] Inventors: Steven P. Mertens, New Hope; Brent C. Gerberding, Minneapolis; David J. Blaeser, Champlin, all of Minn.

[73] Assignee: SciMed Life Systems. Inc., Maple Grove, Minn.

[21] Appl. No.: 08/812,235

[22] Filed: Mar. 6, 1997

Related U.S. Application Data

[63] Continuation-in-part of application No. 08/379,091, Jan. 26, 1995, Pat. No. 5,645,533, which is a continuation of application No. 08/055,695, Apr. 29, 1993, abandoned, which is a continuation-in-part of application No. 07/725,064, Jul. 5, 1991, Pat. No. 5,281,203, and application No. 07/843,647, Feb. 28, 1992, abandoned.

[51] Int. Cl.[6] .................................................. A61M 29/00
[52] U.S. Cl. ............................................. 604/96; 604/243
[58] Field of Search ................................ 604/96, 97, 102, 604/256, 523, 101, 243, 164, 167; 606/192, 194

[56] References Cited

U.S. PATENT DOCUMENTS

| | | |
|---|---|---|
| 3,460,541 | 8/1969 | Doherty . |
| 3,707,151 | 12/1972 | Jackson . |
| 3,889,686 | 6/1975 | Duturbure . |
| 3,890,977 | 6/1975 | Wilson . |
| 3,970,089 | 7/1976 | Saice . |
| 4,194,513 | 3/1980 | Rhine et al. . |
| 4,299,226 | 11/1981 | Banka . |
| 4,364,392 | 12/1982 | Strother et al. . |
| 4,413,989 | 11/1983 | Schjeldahl et al. . |
| 4,423,725 | 1/1984 | Baran et al. . |
| 4,425,919 | 1/1984 | Alston, Jr. et al. . |
| 4,445,892 | 5/1984 | Hussein et al. . |
| 4,554,929 | 11/1985 | Samson et al. . |
| 4,573,470 | 3/1986 | Samson et al. . |
| 4,581,017 | 4/1986 | Sahota . |
| 4,606,347 | 8/1986 | Fogarty et al. . |
| 4,616,653 | 10/1986 | Samson et al. . |

(List continued on next page.)

FOREIGN PATENT DOCUMENTS

| | | |
|---|---|---|
| A-10067/88 | 7/1988 | Australia . |
| 513 818 A1 | 11/1992 | European Pat. Off. . |
| 1251-914 | 5/1984 | U.S.S.R. . |
| WO 92/00775 | 1/1992 | WIPO . |
| WO 92/13589 | 8/1992 | WIPO . |
| WO 93/11826 | 6/1993 | WIPO . |
| WO 94/11047 | 5/1994 | WIPO . |

*Primary Examiner*—Wynn Wood Coggins
*Assistant Examiner*—A. T. Nguyen
*Attorney, Agent, or Firm*—Crompton, Seager & Tufte, LLC

[57] ABSTRACT

A method and apparatus for introducing therapeutic and/or diagnostic devices through a balloon dilatation catheter and to an occlusion site, while longitudinally moving the dilatation balloon proximally from the occlusion area. This may enable, for example, an Intra-Vascular Ultra-Sonic (IVUS) device to produce non-distorted images of an occluded site between balloon dilatations of an angioplasty procedure.

14 Claims, 7 Drawing Sheets

U.S. PATENT DOCUMENTS

| | | |
|---|---|---|
| 4,641,654 | 2/1987 | Samson et al. . |
| 4,646,742 | 3/1987 | Packard et al. . |
| 4,654,025 | 3/1987 | Cassou et al. . |
| 4,655,746 | 4/1987 | Daniels et al. . |
| 4,723,550 | 2/1988 | Bales et al. . |
| 4,748,982 | 6/1988 | Horzewski et al. . |
| 4,762,129 | 8/1988 | Bonzel . |
| 4,763,654 | 8/1988 | Jang . |
| 4,771,777 | 9/1988 | Horzewski et al. . |
| 4,790,315 | 12/1988 | Mueller, Jr. et al. . |
| 4,798,193 | 1/1989 | Giesy et al. . |
| 4,798,594 | 1/1989 | Hillstead . |
| 4,813,934 | 3/1989 | Engelson et al. . |
| 4,817,613 | 4/1989 | Jaraczewski et al. . |
| 4,838,268 | 6/1989 | Keith et al. . |
| 4,846,174 | 7/1989 | Willard et al. . |
| 4,846,193 | 7/1989 | Tremulis et al. . |
| 4,848,344 | 7/1989 | Sos et al. . |
| 4,877,031 | 10/1989 | Conway et al. . |
| 4,892,519 | 1/1990 | Songer et al. . |
| 4,898,577 | 2/1990 | Badger et al. . |
| 4,906,241 | 3/1990 | Noddin et al. . |
| 4,928,693 | 5/1990 | Goodin et al. . |
| 4,932,413 | 6/1990 | Shockey et al. . |
| 4,932,959 | 6/1990 | Horzewski et al. . |
| 4,944,745 | 7/1990 | Sogard et al. . |
| 4,964,409 | 10/1990 | Tremulis . |
| 4,967,753 | 11/1990 | Haase et al. . |
| 4,976,720 | 12/1990 | Machold et al. . |
| 4,986,814 | 1/1991 | Burney et al. . |
| 4,988,356 | 1/1991 | Crittenden et al. . |
| 4,994,027 | 2/1991 | Farrell . |
| 4,998,917 | 3/1991 | Gaiser et al. . |
| 5,003,990 | 4/1991 | Osypka . |
| 5,007,901 | 4/1991 | Shields . |
| 5,015,231 | 5/1991 | Keith et al. . |
| 5,019,042 | 5/1991 | Sahota . |
| 5,026,607 | 6/1991 | Kiezulas . |
| 5,031,636 | 7/1991 | Gambale et al. . |
| 5,032,113 | 7/1991 | Burns . |
| 5,035,494 | 7/1991 | Engelson et al. . |
| 5,035,694 | 7/1991 | Kasprzyk et al. ............... 604/96 X |
| 5,035,705 | 7/1991 | Burns . |
| 5,040,548 | 8/1991 | Yock .................. 604/96 X |
| 5,045,061 | 9/1991 | Seifert et al. . |
| 5,046,497 | 9/1991 | Millar . |
| 5,047,018 | 9/1991 | Gay et al. . |
| 5,047,045 | 9/1991 | Arney et al. . |
| 5,057,092 | 10/1991 | Webster, Jr. . |
| 5,061,267 | 10/1991 | Zeiher . |
| 5,061,273 | 10/1991 | Yock . |
| 5,066,285 | 11/1991 | Hillstead . |
| 5,078,681 | 1/1992 | Kawashima . |
| 5,085,636 | 2/1992 | Burns . |
| 5,090,958 | 2/1992 | Sahota . |
| 5,114,403 | 5/1992 | Clarke et al. . |
| 5,117,831 | 6/1992 | Jang et al. . |
| 5,120,308 | 6/1992 | Hess . |
| 5,125,905 | 6/1992 | Wright et al. . |
| 5,135,494 | 8/1992 | Engelson et al. . |
| 5,135,535 | 8/1992 | Kramer . |
| 5,137,513 | 8/1992 | McInnes et al. . |
| 5,141,518 | 8/1992 | Hess et al. . |
| 5,147,377 | 9/1992 | Sahota . |
| 5,154,725 | 10/1992 | Leopold . |
| 5,160,321 | 11/1992 | Sahota . |
| 5,171,221 | 12/1992 | Samson . |
| 5,171,222 | 12/1992 | Euteneuer et al. . |
| 5,171,298 | 12/1992 | Walker et al. . |
| 5,180,367 | 1/1993 | Kontos et al. ..................... 604/101 |
| 5,181,921 | 1/1993 | Makita et al. . |
| 5,190,046 | 3/1993 | Shturman ............... 604/96 X |
| 5,195,971 | 3/1993 | Sirhan . |
| 5,209,728 | 5/1993 | Kraus et al. . |
| 5,217,434 | 6/1993 | Arney . |
| 5,217,482 | 6/1993 | Keith . |
| 5,221,260 | 6/1993 | Burns et al. . |
| 5,250,034 | 10/1993 | Appling et al. . |
| 5,256,144 | 10/1993 | Kraus et al. . |
| 5,259,839 | 11/1993 | Burns . |
| 5,263,932 | 11/1993 | Jang . |
| 5,265,622 | 11/1993 | Barbere . |
| 5,269,793 | 12/1993 | Simpson . |
| 5,279,562 | 1/1994 | Sirhan et al. . |
| 5,281,200 | 1/1994 | Corso, Jr. et al. . |
| 5,281,203 | 1/1994 | Ressemann . |
| 5,290,247 | 3/1994 | Crittenden . |
| 5,300,025 | 4/1994 | Wantink . |
| 5,304,198 | 4/1994 | Samson . |
| 5,305,740 | 4/1994 | Kolobow . |
| 5,312,340 | 5/1994 | Keith . |
| 5,318,529 | 6/1994 | Kontos . |
| 5,320,604 | 6/1994 | Walker et al. . |
| 5,324,259 | 6/1994 | Taylor et al. . |
| 5,334,154 | 8/1994 | Samson et al. . |
| 5,344,402 | 9/1994 | Crocker . |
| 5,348,537 | 9/1994 | Wiesner et al. . |
| 5,364,347 | 11/1994 | Jang . |
| 5,364,354 | 11/1994 | Walker et al. . |
| 5,383,890 | 1/1995 | Miraki et al. . |
| 5,582,178 | 12/1996 | Yock . |

CATHETER HAVING EXTENDABLE GUIDE WIRE LUMEN

RELATION TO OTHER APPLICATIONS

This application is a continuation-in-part of U.S. patent application Ser. No. 08/379,091, filed Jan. 26, 1995, now U.S. Pat. No. 5,645,533 which is a continuation of U.S. Ser. No. 08/055,695, filed Apr. 29, 1993, which is a continuation-in-part of U.S. patent application Ser. No. 07/725,064, filed Jul. 5, 1991, now U.S. Pat. No. 5,281,203, and U.S. patent application Ser. No. 07/843,647, filed Feb. 28, 1992, now abandoned, the entire disclosures of which are specifically incorporated herein by reference.

FIELD OF THE INVENTION

The present invention relates generally to methods and devices used in intravascular therapeutic and diagnostic procedures. More particularly, the present invention relates to methods and apparatus for providing therapeutic and/or diagnostic devices to a desired vascular site through a dilation balloon catheter, while allowing the dilatation balloon catheter to be withdrawn from the desired area.

BACKGROUND OF THE INVENTION

Intravascular therapeutic techniques, such as angioplasty procedures, have been developed as alternatives to bypass surgery for treating vascular diseases or other conditions that occlude or reduce the lumen size of portions of a patient's vascular system. During a balloon angioplasty procedure, a balloon catheter is typically inserted intravascularly into a patient through a relatively small puncture, which may be located proximate the groin, and navigated by a treating physician to the occluded vascular site.

A balloon catheter typically includes a balloon or dilating member at the distal end which is placed adjacent the vascular occlusion. Intravascular inflation of the dilating member by sufficient pressures, on the order of 5 to 12 atmospheres or so, causes the balloon to displace the occluding matter. It is known that a number of sequential balloon dilatations may be required to properly revascularize the occluded lumen and restore substantially normal blood flow therethrough. Because the effectiveness of any one balloon dilatation may not be known, it is desirable to view the vascular site after selected balloon dilations to monitor the progress and to determine if any adjustments should be made to the procedure.

One known method for viewing the vascular site is to inject a radiopaque die into the patient's vasculature. X-rays or the like may then be used to view the revascularized portion of the vessel. A disadvantage of this approach is that extended exposure to X-rays can be harmful to both the patient and the treating personnel.

Another more recent approach for viewing occluded sites during an angioplasty procedure is to use an Intra-Vascular Ultra-Sonic (IVUS) device that is attached to the distal end of a guide member, guide wire or the like. The IVUS device can be advanced down the guide wire lumen of a balloon dilatation catheter until the IVUS device is adjacent the dilatation balloon. After a selected balloon dilatation, the IVUS device may provide an image of the revascularized portion of the vessel. A limitation of this approach is that the dilatation balloon often distorts the ultra-sonic image of the vessel, and thus the usefulness of the images provided by the IVUS device are negated.

SUMMARY OF THE INVENTION

The present invention overcomes many of the limitations of the prior art by providing a method and apparatus for introducing therapeutic and/or diagnostic devices through a balloon dilatation catheter and to an occluded vessel, while allowing the balloon dilatation catheter to be withdrawn from the desired area. This may enable, for example an Intra-Vascular Ultra-Sonic (IVUS) device, to produce non-distorted images of a revascularized portion of a vessel.

In accordance with the present invention, a longitudinally extendable guide member is provided in a balloon dilatation catheter. Positioned within the longitudinally extendable guide member is preferably a therapeutic and/or diagnostic device, such as an IVUS device. During an angioplasty procedure, the balloon is positioned adjacent an occluded site and inflated to dilate the occluding matter. Thereafter, and to view the revascularized portion of the vessel, the IVUS device may be advanced down the extendable guide member until the IVUS device is adjacent the desired site.

Thereafter, the balloon dilatation catheter may be pulled proximally relative to the extendable guide member. Thus, the dilatation balloon is effectively moved proximally away from the IVUS device, while the IVUS device remains adjacent the revascularized portion of the vessel. That is, and in a preferred embodiment, the extendable guide wire lumen member and the IVUS device remain substantially stationary relative to the revascularized portion of the vessel. The IVUS device may then be used to provide an image of the revascularized portion of the vessel. It is noted that the extendable guide member may provide protection to the IVUS device while the balloon dilatation catheter is withdrawn proximally therefrom.

Because the extendable guide member remains across the occluded site or lesion, the balloon catheter may easily be repositioned across the site by simply re-advancing the balloon catheter over the extendable guide member. This configuration provides an efficient means for dilating a vessel with a dilation balloon, and imaging the vessel between selected dilatations.

In a first illustrative embodiment of the present invention, the balloon dilatation catheter includes an inflation tube with an inflation lumen extending therethrough. Attached to a distal end portion of the inflation tube is an inflatable balloon. The interior of the inflatable balloon is in fluid communication with the inflation lumen of the inflation tube. In this configuration, the inflatable balloon can be expanded by applying pressure to the inflation lumen.

To provide a longitudinally extending guide wire lumen, an elongated guide member preferably coextends interiorly within at least a portion of the inflation lumen of the balloon catheter, and is in a slidable relation therewith. The elongated guide member is also adapted to slidably receive an elongated device such as an IVUS device. Because the elongated guide member coextends interiorly within at least a portion of the inflation lumen, a sealing means is provided in the balloon catheter. The sealing means slidably receives the guide member and provides a seal between the inflation lumen and the exterior of the intravascular catheter. The seal thus allows the guide member to be longitudinally slidable relative to the balloon catheter while enabling the dilatation balloon to be inflated when desired.

In a preferred embodiment, the sealing means comprises a seal between the inflation tube and the guide member. In this configuration, the guide member may be slidably positioned relative to the dilatation balloon. In addition, an IVUS device that is positioned within the guide member may be slidably positioned relative to the dilatation balloon, and in particular, selectively positioned distally of the dilatation balloon.

In accordance therewith, a number of methods are disclosed for imaging a selected portion of a vessel during an angioplasty procedure. A first illustrative method includes the steps of: providing a catheter that has a movable guide member therein and a balloon located on the distal end thereof, wherein the catheter is positioned within the body such that the balloon is located adjacent the selected portion of the vessel; providing an elongated device that has an imaging device located near the distal end thereof, wherein the elongated device is positioned within the guide member; moving the catheter proximally of the selected portion of the vessel while leaving the movable guide member substantially stationary relative to the selected portion of the vessel; positioning the elongated device adjacent the selected portion of the vessel; and imaging the selected portion of the vessel with the imaging device.

In another illustrative embodiment of the present invention, a standard balloon catheter is combined with a lumen extension device. The lumen extension device is a separate device that is used in conjunction with a catheter that has a guide wire lumen therein. The lumen extension device allows a user to selectively extend the guide wire lumen of a conventional catheter.

In an illustrative embodiment, the lumen extension device includes an elongated guide member for slidably receiving an elongated device, such as an IVUS device. The guide member is adapted to be slidably disposed within the guide wire lumen of the standard catheter. Attached to the proximal end of the guide member is a housing. The housing preferably engages the proximal end of the catheter, and has a control mechanism for controlling the relative longitudinal position of the guide member relative to the catheter. Preferably, the catheter has a manifold on the proximal end thereof, and the housing is attached to the manifold.

In accordance therewith, another illustrative method is contemplated including the steps of: providing a catheter that has a guide wire lumen extending longitudinally therethrough, and a balloon located on the distal end thereof, wherein the catheter is inserted into the body such that the balloon is positioned adjacent to the selected portion of the vessel; providing a lumen extension device comprising an elongated tube, wherein the lumen extension device is slidably positioned within the guide wire lumen of the catheter; providing an elongated device that has an imaging device located near the distal end thereof, wherein the elongated device is positioned within the elongated tube of the lumen extension device; moving the catheter proximally of the selected portion of the vessel while leaving the guide member of the lumen extension device substantially stationary relative to the selected portion of the vessel; positioning the elongated device adjacent the selected portion of the vessel; and imaging the selected portion of the vessel with the imaging device.

The present invention, together with further objects and advantages, will be best understood by reference to the following detailed description taken in conjunction with the accompanying drawings.

DETAILED DESCRIPTION OF THE PREFERRED EMBODIMENT

The presently preferred embodiments and methodology described herein are applicable to coronary angioplasty procedures and are specifically described in the context of dilation balloon catheters. It should be understood, however, that the embodiments and methodology of the present invention may be adapted for use with other types of intravascular therapeutic devices, such as atherectomy catheters, as well as diagnostic catheters, such as ultrasonic catheters.

Figure 1:
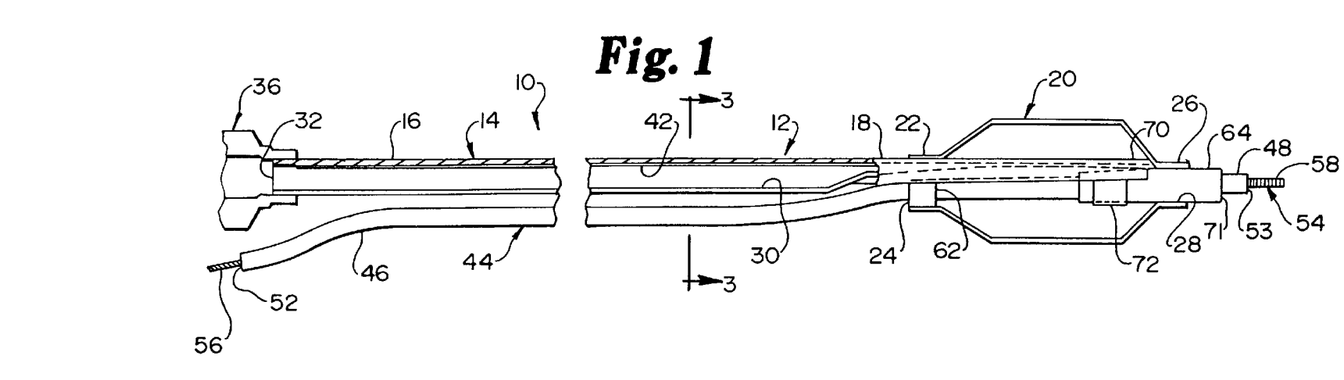
FIG. 1 is a side view, partially in section, of a preferred embodiment of a balloon dilation catheter of the present invention.

Referring to FIG. 1, a first embodiment of a single-operator exchange type intravascular apparatus is indicated generally at 10. The intravascular apparatus 10 includes a balloon dilation catheter 12 having an elongated shaft 14. A proximal portion 16 of the shaft 14 is adapted to extend outside the body of a patient during use, and a distal portion 18 of the shaft 14 is positionable intravascularly during use by manipulation of the proximal portion 16.

A dilation balloon 20 is located at and connected to the distal portion 18 of the catheter shaft 14. The balloon 20 can be formed from a polyolefin copolymer or other polymer material. For example, in one embodiment, the balloon 20 is formed of a polyolefin copolymer (such as that sold by DuPont under the tradename SURLYN as Resin No. 8527) using secondary treatment with 5 to 50 Mega-rad electron beam irradiation to enhance strength in the region of the balloon 20. Preferably, the balloon 20 has a proximal neck portion 22 defining a proximal opening 24, and a distal neck portion 26 defining a distal opening 28. The proximal neck portion 22 preferably has an outer diameter of about 0.040 inches and an inner diameter of about 0.034 inches. The distal neck portion 26 preferably has an outer diameter of about 0.030 inches and an inner diameter of about 0.025 inches.

The distal portion 18 of the shaft 14 extends into the proximal opening 24 in the balloon 20 and is preferably connected to the proximal neck portion 22. The shaft 14 includes an inflation lumen 30 extending therethrough and has a proximal opening 32 and a distal opening 34. A manifold 36 is connected to the proximal portion 16 of the shaft 14 and the dilation balloon 20 is in fluid flow communication with the inflation lumen 30. Inflation fluid is conveyed via the lumen 30 from the manifold 36 to inflate the balloon 20 and therefore dilate a vessel in a conventional manner known in the art.

Figure 2:
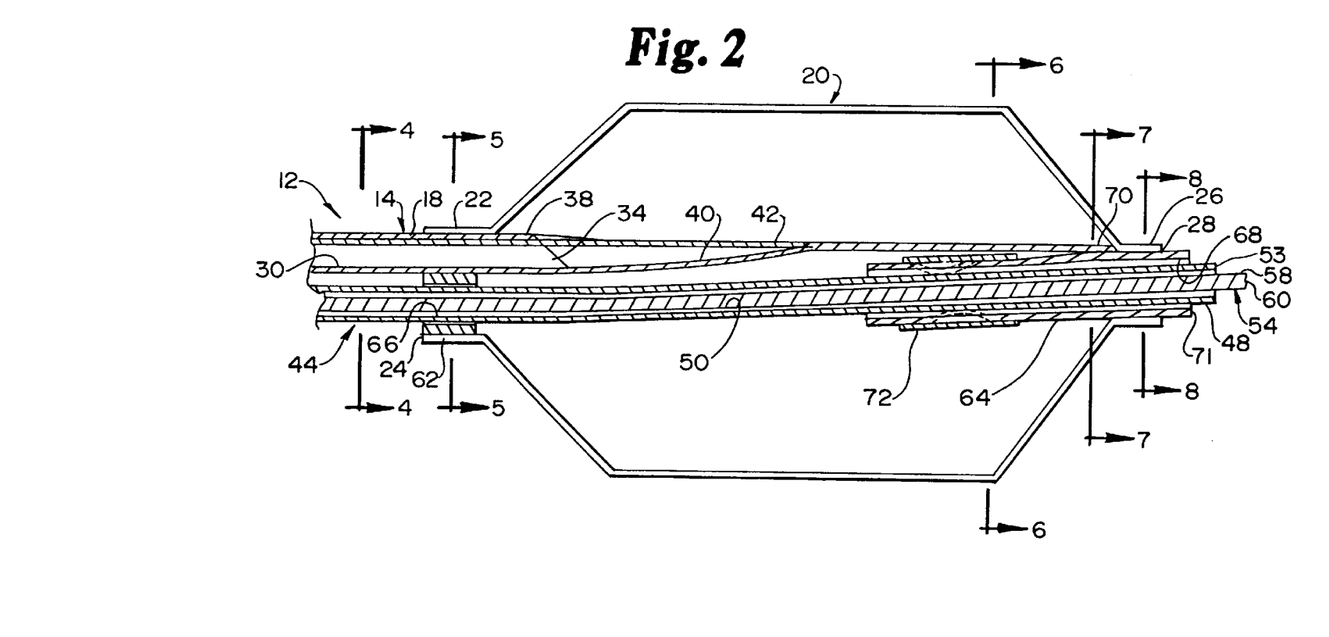
FIG. 2 is a longitudinal sectional view of a distal portion of the catheter shown in FIG. 1.
Figure 3:
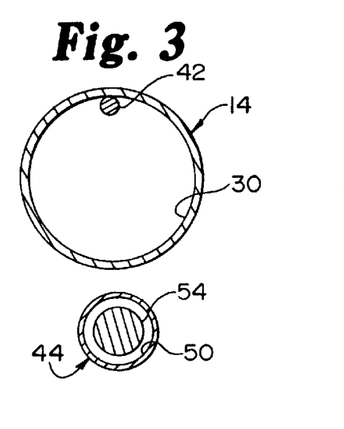
FIG. 3 is a cross-sectional view of the catheter taken along the line 3—3 in FIG. 1.
Figure 4:
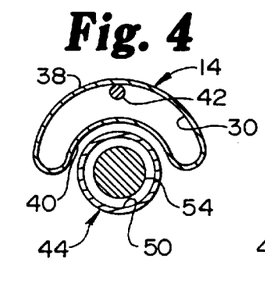
FIG. 4 is a cross-sectional view of the catheter taken along the line 4—4 in FIG. 2.
Figure 5:
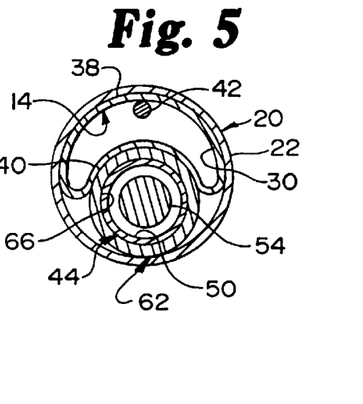
FIG. 5 is a cross-sectional view of the catheter taken along the line 5—5 in FIG. 2.
Figure 6:
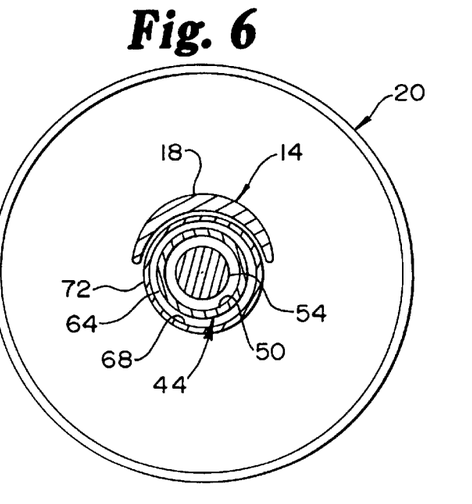
FIG. 6 is a cross-sectional view of the catheter taken along the line 6—6 of FIG. 2.
Figure 7:
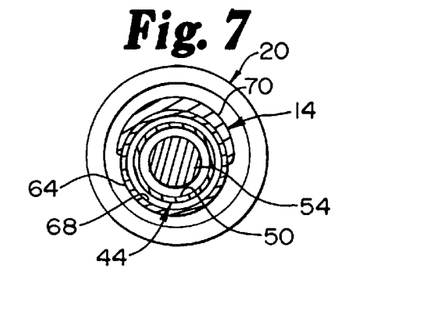
FIG. 7 is a cross-sectional view of the catheter taken along the line 7—7 of FIG. 2.
Figure 8:
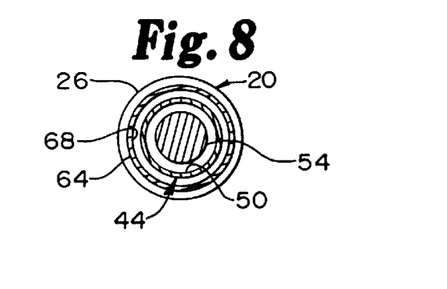
FIG. 8 is a cross-sectional view of the catheter taken along the line 8—8 of FIG. 2.

In a preferred embodiment, the shaft 14 has a length of approximately 135 cm. The proximal portion 16 of the shaft 14 is preferably made of stainless steel hypodermic tubing and the distal portion 18 is made of a relatively flexible polymeric material such as a polyolefin copolymer or polyethylene. This type of shaft is disclosed in U.S. patent application Ser. No. 07/833,099, filed Feb. 10, 1992, the disclosure of which is specifically incorporated herein by reference. In order to minimize the profile of the distal portion 18 of shaft 14, the shape of the shaft 14 and lumen 30 converges from a circular cross-section at the proximal portion 16 thereof (FIG. 3) to a kidney-shaped cross section at the distal portion thereof (FIGS. 4–6). An upper wall 38 and a lower wall 40 of the shaft 14 converge distally of the distal opening 34 in the lumen 30 and extend across the balloon 20 to a position adjacent the distal neck portion 26 of the balloon 20. Preferably, a stiffening wire 42 extends distally from a distal end of the steel tubing and is attached to a distal end of the balloon 20 as disclosed in the '113 patent to provide additional support for the manipulation of the catheter 12. Alternatively, the stiffening wire 42 can be attached to an underside of the upper wall 38 of the shaft and extend to approximately the center of the balloon 20 as shown in FIGS. 1 and 2.

To facilitate the operation and exchange of the components of the intravascular apparatus 10, an elongated guide lumen 44 is adapted to extend through the proximal and distal openings 24 and 28 of the balloon 20 for slidable movement relative to the balloon 20 during use. The guide lumen 44 also has an inner chamber 50 extending therethrough from a proximal end 52 to a distal end 53 thereof for slidably receiving a conventional guide wire 54. The guide lumen 44 has a sufficient length, preferably about 135 cm, so that a proximal portion 46 of the guide lumen 44 can extend outside the body of a patient during use while a distal portion 48 extends distally of the balloon 20. Preferably, the guide lumen 44 is approximately the same length as a conventional catheter.

The guide lumen 44 may also be provided in different sizes to accommodate different size devices. For example, the guide lumen 44 can be provided with an inner diameter of 0.017 inches and an outer diameter of 0.020 inches for use with a 0.014 inch guide wire. For use with a 0.010 inch guide wire, the guide lumen 44 may be provided with an inner diameter of 0.013 inches and an outer diameter of 0.016 inches.

Preferably, the guide lumen 44 is made of a polymeric material, such as polyimide, and has a low friction coating, such as Teflon®, on both the inner and outer surfaces thereof. A coating on the inner surface enhances guide wire movement through the chamber 50, and a coating on the outer surface enhances movement of the guide lumen 44 through a guiding catheter, a vessel, or the balloon 20. Alternatively, the guide lumen 44 can be made of other materials, such as polyurethane, polyester, or other polymers. The guide lumen 44 can also be made of a polyimide-teflon composite material, or reinforced with wire or a braid of metal or plastic or other materials.

To provide greater stiffness at the proximal portion 46 of the guide lumen 44 compared to the distal portion 48, the pitch of a wound reinforcing wire can be varied a desired amount along the length of the guide lumen 44. The variable pitch wire can provide increased stiffness at the proximal portion 46 of the guide lumen 44 to facilitate manipulation of the entire guide lumen 44. The variable pitch wire can also provide sufficient flexibility at the distal portion 48 of the guide lumen 44 to allow the guide lumen 44 to easily follow the guide wire 54 through a vessel. Also alternatively, the coatings may be made of other materials such as a hydrophilic or silicone coating. In addition to or instead of the low friction coating, a metallic or foil coating may also be incorporated on the inner or outer surface of the guide lumen 44.

The guide wire 54 has a sufficient length, preferably about 160–190 cm, so that a proximal portion 56 of the guide wire 54 can extend outside the body of a patient from an opening in the proximal end 52 in the guide lumen 44 while a distal portion 58 extends distally from an opening in the distal end 53 of the guide lumen 44. The proximal portion 56 of the guide wire 54 can also extend out of an opening in the guide lumen located distally of the proximal end 52 of the guide lumen 44. In addition, the guide wire 54 can have an outer diameter between 0.008 and 0.022 inches, although conventional guide wires typically have a diameter of 0.010, 0.014 or 0.018 inches.

In a first embodiment, a proximal seal member 62 is sealingly connected to the proximal neck portion 22 of the balloon 20 and a distal seal member 64 is sealingly connected to the distal neck portion 26 of the balloon 20. The proximal and distal seal members 62 and 64 have passageways 66 and 68 therethrough for slidably receiving the guide lumen 44. The seal members 62 and 64 are preferably configured as collars and are made of a polymeric material, such as polyimide, polyurethane, polyester or the like. An upper portion of the proximal seal member 62 is attached to the curved bottom wall 40 of the catheter shaft 14, and a lower portion is attached to the proximal neck portion 22 of the balloon 20. The entire periphery of the distal seal member 64 is attached to the distal neck portion 26, and a distal end 70 of the shaft 14 is attached to a top portion of the distal seal member 64 proximally of the neck portion 26.

In use, the distal portion 48 of the guide lumen 44 is adapted to extend distally from an end 71 of the distal seal member 64 while the proximal portion 46 is outside the body of a patient. Preferably, the outer diameter of the guide lumen 44 is only slightly smaller than the inner diameters of the proximal and distal seal members 62 and 64 to create a tolerance fit which allows slidable movement of the guide lumen 44 through the seal member passageways 66 and 68. When the balloon 20 is inflated with fluid, the tolerance fit between the guide lumen 44 and the proximal and distal seal members 62 and 64 inhibits inflation fluid from exiting the balloon 20.

In addition, the distal seal member 64 preferably extends proximally into the balloon 20 and has an expandable, tubular valve member 72 made of an elastomeric material such as TECOTHANE or the like. As shown in dashed lines in FIG. 2, the valve member 72 expands radially inward against the guide lumen 44 when the balloon 20 is inflated to further seal any space between the guide lumen 44 and the distal seal member 64. A valve member of similar construction can also be incorporated into the proximal seal member 62 if desired.

In accordance with the present invention, a longitudinally extendable guide lumen 44 is provided in the distal seal member 64. Positioned within the longitudinally extendable guide lumen 44 is preferably a therapeutic and/or diagnostic device 54, such as an IVUS device. During an angioplasty procedure, the balloon 20 is positioned adjacent an occluded site and inflated to dilate the occluding matter. Thereafter, the intravascular apparatus 10 may be withdrawn relative to the vessel while the guide lumen 44 and the IVUS device 54 may remain substantially at the revascularized portion of the vessel. Thus, the dilatation balloon 20 may be effectively moved proximally away from the IVUS device 54 and the guide lumen 44, while the IVUS device 54 and the guide lumen 44 remain substantially adjacent the revascularized portion of the vessel. The IVUS device 54 may then be used to provide an image of the revascularized portion of the vessel. It is noted that the extendable guide lumen 44 may provide protection to the IVUS device 54 while the intravascular apparatus 10 is withdrawn proximally therefrom.

In addition, and because the extendable guide lumen 44 remains substantially across the occluded site or lesion, the intravascular apparatus 10 may easily be repositioned across the site by simply advancing the intravascular apparatus 10 over the extendable guide lumen 44. This configuration provides an efficient means for dilating a vessel with a dilation balloon, and imaging the vessel between selected dilatations.

FIGS. 9–19 illustrate alternative embodiments of the present invention. Since these embodiments are similar to the previously described embodiment, similar parts appearing in FIGS. 9–19 are represented by the same, corresponding reference numeral, except for the corresponding letter in the numerals of the latter.

Figure 9:
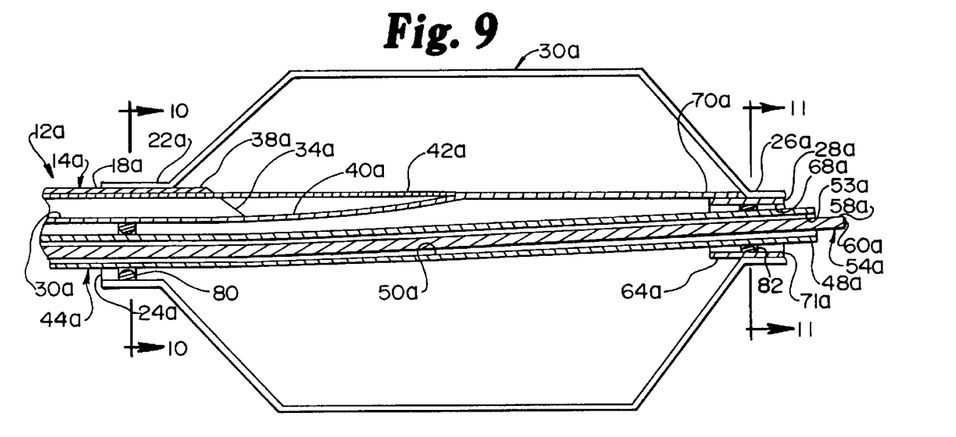
FIG. 9 is a longitudinal sectional view of a second preferred embodiment of a balloon dilation catheter.
Figure 10:
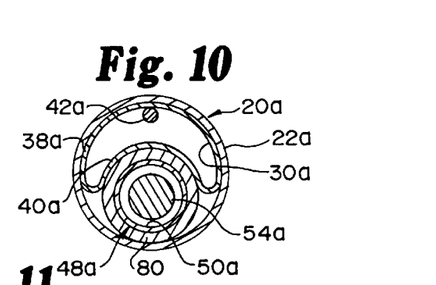
FIG. 10 is a cross-sectional view of the second preferred embodiment taken along the line 10—10 in FIG. 9.
Figure 11:
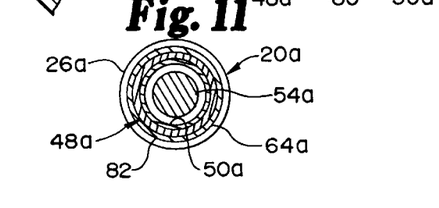
FIG. 11 is a cross-sectional view of the second preferred embodiment taken along the line 11—11 in FIG. 9.

In the embodiment shown in FIGS. 9–11, a pair of split O-ring type seals are provided to prevent inflation fluid from exiting the balloon 20a. An upper portion of a proximal split O-ring 80 is attached to the curved bottom wall 40a of the catheter shaft 14a, and a lower portion is attached to the proximal neck portion 22a of the balloon 20a. The entire periphery of a distal O-ring 82 can be attached to the distal seal member 64a as shown in FIG. 9 or bonded directly to the distal neck portion 26a of the balloon 20. The split O-rings 80 and 82 are preferably made of a relatively soft durometer urethane material or the like and can be preformed or molded into the balloon 20a.

In a molding operation, a polyurethane adhesive or the like can be injected into a shaped mold temporarily positioned in the neck portion of the balloon 20a. Although the contact surfaces of the O-rings 80 and 82 are shown as rounded surfaces, the O-rings can be formed in any desired shape to facilitate slidable movement of the guide lumen 44a while providing an effective seal when the balloon 20a is inflated. The shape and material of the O-ring allows greater deformation as a result of pressure from the inflation fluid, which may provide a more effective seal. Moreover, the "single point" contact of the proximal and distal O-rings 80 and 82 with the guide lumen 44a may facilitate advancement and withdrawal of the catheter 12a over the guide lumen 44a because the decreased contact area tends to reduce frictional forces acting on the guide lumen 44a.

Figure 12:
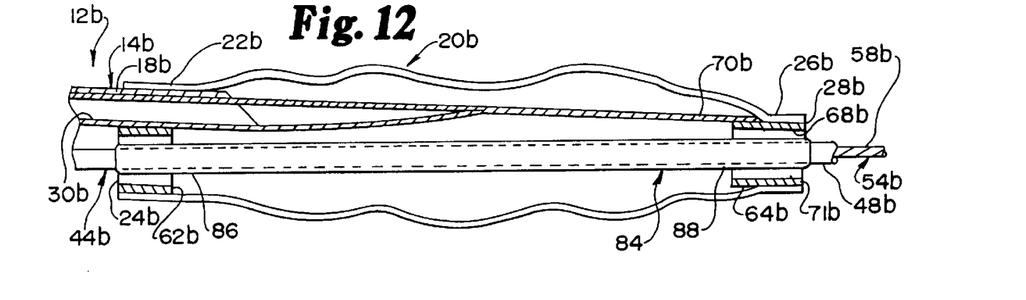
FIG. 12 is a side view, partially in section, of a third preferred embodiment of a balloon dilation catheter showing a deflated balloon.
Figure 13:
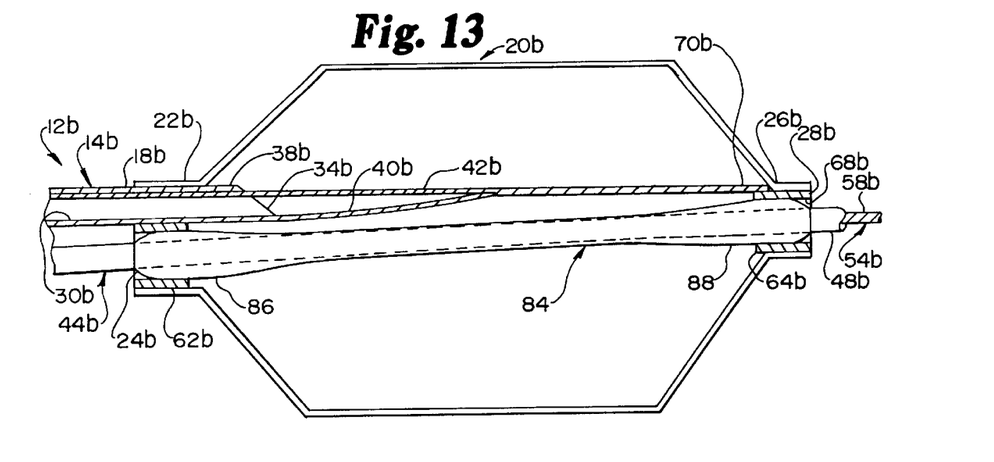
FIG. 13 is a side view, partially in section, of the embodiment in FIG. 12 showing an inflated balloon.

In the embodiment shown in FIGS. 12–13, the guide lumen 44b is configured with an enclosed, deformable bladder-type sheath 84 surrounding a portion thereof. The sheath 84 has a constant volume of fluid therein (not shown) and is approximately the same length as the distance between the proximal and distal seal members 62b and 64b of the balloon 20b. Prior to inflation of the balloon 20b, the guide lumen 44b is advanced or withdrawn until proximal and distal end portions 86 and 88 of the sheath 84 are substantially aligned with the proximal and distal seal members 62b and 64b (FIG. 12). When the balloon 20b is inflated with fluid, the fluid in the sheath 84 is displaced outwardly toward the end portions 86 and 88 (FIG. 13). As a result, the volume of space occupied by the end portions 86 and 88 increases such that the end portions bear against the seal members 62b and 64b to create an effective seal which prevents the inflation fluid from exiting the balloon 20b.

Figure 14:
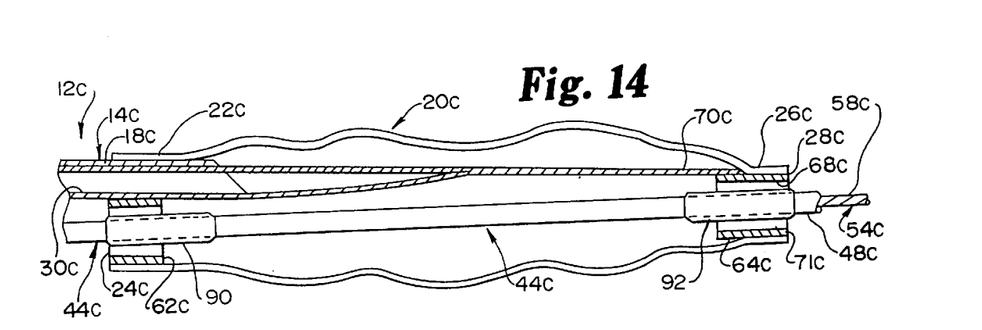
FIG. 14 is a side view, partially in section, of a fourth preferred embodiment of a balloon dilation catheter showing a deflated balloon.
Figure 15:
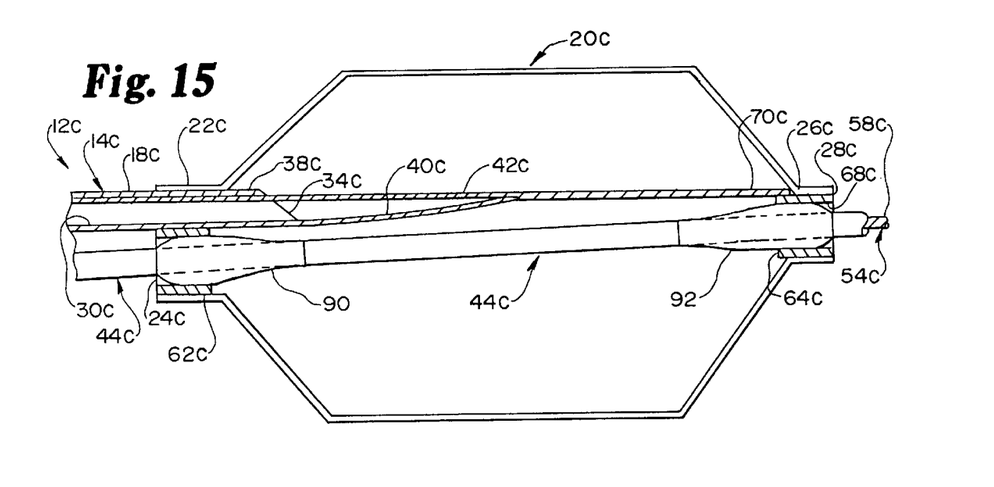
FIG. 15 is a side view, partially in section, of the embodiment in FIG. 14 showing an inflated balloon.

Alternatively, the sheath 84b can be provided in the form of spaced apart proximal and distal sheaths 90 and 92 surrounding the guide lumen 44c as shown in FIGS. 14 and 15. The distance between the sheaths 90 and 92 is approximately the same as the distance between the seal members 62c and 64c. The sheaths 90 and 92 are aligned with the corresponding seal members 62c and 64c prior to inflation of the balloon 20c (FIG. 14), and the inflation fluid displaces the fluid in the sheaths 90 and 92 outwardly to create a seal between the sheaths 90 and 92 and the corresponding seal members 62c and 64c. In either of the embodiments shown in FIGS. 12–15, the seal members can be eliminated and the sheaths can be configured to bear directly against the corresponding neck portions of the balloon when displaced by the inflation fluid.

Alternatively, a bladder-type valve member which surrounds the guide lumen 44 and expands when filled with fluid can provide an active seal. Valve members of this type are disclosed in U.S. Pat. No. 5,085,636, issued Feb. 4, 1992, the disclosure of which is specifically incorporated herein by reference. Such a seal could be activated by the inflation fluid which fills the balloon 20 or by a separate flow of fluid through a micro-tube connected to the bladder.

Figure 9A:
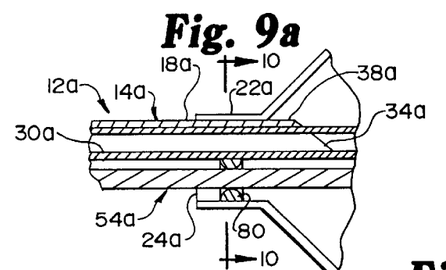
FIG. 9A is a longitudinal sectional view of an alternative embodiment of the catheter shown in FIG. 9.

In any of the embodiments described herein, the proximal and distal seal members can be configured to slidably receive and provide an effective seal around a guide wire without the use of a guide lumen (see, e.g., FIG. 9A). One advantage of this configuration may be the reduced profile of the balloon 20 resulting from the elimination of an inner tube inside the balloon 20. Such a configuration may also facilitate the flow of a radiopaque dye solution which is typically introduced into the vessel after an angioplasty procedure to determine whether an acceptable blood flow has been established through the vessel. When a 0.014 inch guide wire is used, the proximal neck portion 22 preferably has an outer diameter of about 0.036 inches and an inner diameter of about 0.030 inches. The distal neck portion 26 preferably has an outer diameter of about 0.025 inches and an inner diameter of about 0.020 inches. Thus, the distal and proximal seals inhibit fluid from exiting the balloon 20 without separating the movable guide wire from the inflation fluid in the balloon.

FIGS. 16–19 illustrate yet another embodiment of the present invention. In this embodiment, the shaft 14d has a relatively large diameter body portion 100 and a smaller diameter distal end portion 102 which extends through the proximal and distal openings 24d and 28d in the balloon 20d. Preferably, the juncture of the body portion 100 and the distal end portion 102 is defined by a tapered shoulder 103 adjacent the balloon 20d. The distal end portion 102 of shaft 14d is sealingly attached to the proximal and distal neck portions 22d and 26d of the balloon 20d. The balloon 20d is inflated by conveying fluid via the inflation lumen 30d of the shaft 14d through a plurality of openings 104 formed in the distal end portion 102 of the shaft. Instead of slidably attaching the guide lumen 44d to the balloon 20d and positioning the entire guide lumen 44d outside the shaft 14d, a portion of the guide lumen 44d is movably positioned within a distal portion of the inflation lumen 30d of shaft 14d. Because the guide lumen 44d is positioned within the reduced diameter shaft lumen 30d rather than outside the shaft 14d, the profile of catheter 12d is minimized to allow insertion into relatively small vessels. The constant outer diameter of the distal end portion 102 of the shaft 14d also may provide a better joint between the balloon 20d and the shaft 14d.

Figures 16, 17, 18, 19:
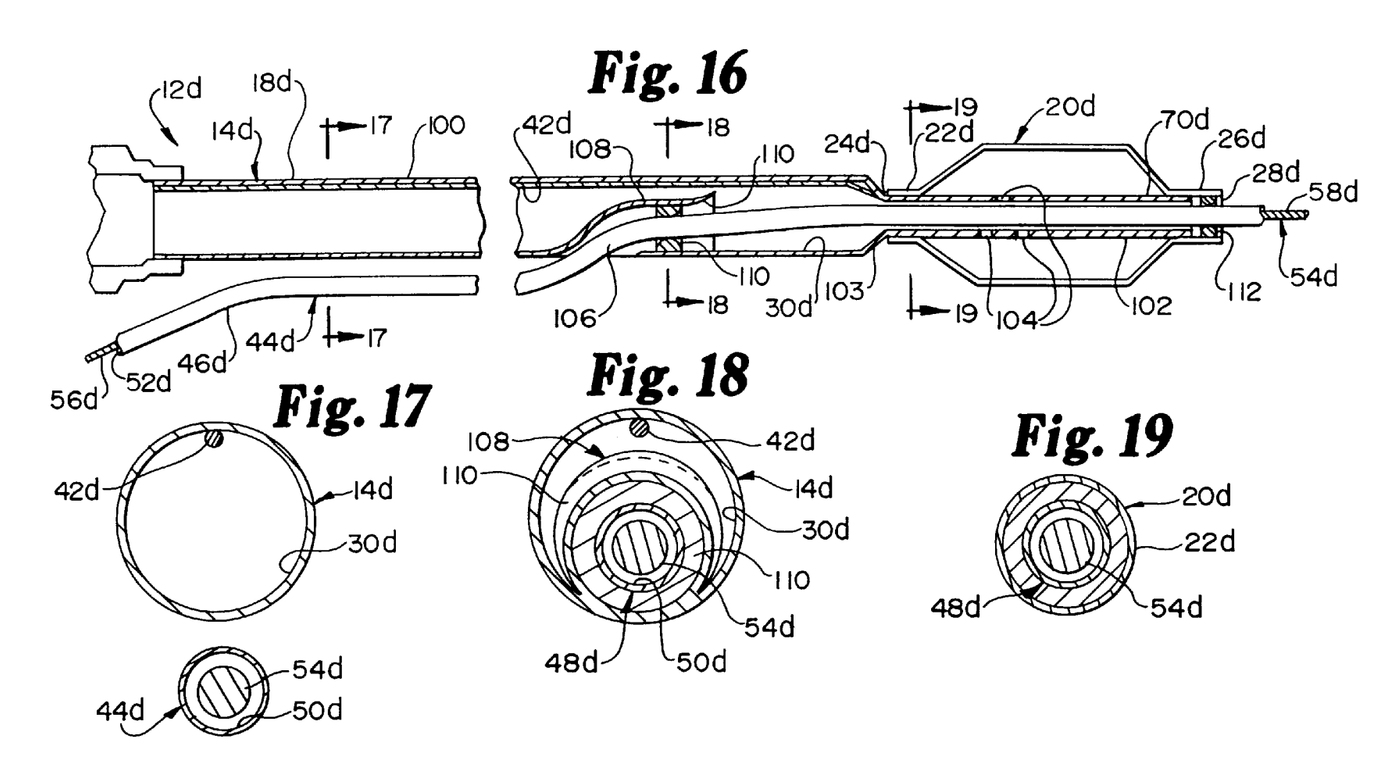
FIG. 16 is a side view, partially in section, of a fifth preferred embodiment of a balloon dilatation catheter.
FIG. 17 is a cross-sectional view of the catheter taken along the line 17—17 in FIG. 16.
FIG. 18 is a cross-sectional view of the catheter taken along the line 18—18 in FIG. 16.
FIG. 19 is a cross-sectional view of the catheter taken along the line 19—19 in FIG. 16.

An opening 106 is provided in the body portion 100 of the shaft 14d, preferably about 10–30 cm proximally from the balloon 20d, for receiving the guide lumen 44d. The guide lumen 44d is guided by an inner core 108 which extends distally a relatively short distance, preferably about 5–15 mm, into the inflation lumen 30d from the opening 106. An end portion 110 of the core 108 is flared to direct the guide lumen 44d into the core 108 when the guide lumen 44d is inserted in a proximal direction through the distal end portion 102 of the shaft 14d. To prevent fluid from exiting through the core 108 and out the opening 106, a seal member 110 is sealingly connected to the core 108. The seal member 110 is preferably a split O-ring type seal which is described in more detail above. A split O-ring type seal member 112 can also be provided in the distal neck portion 26d for sealingly engaging the guide lumen 44d.

Alternatively, the opening 106 and core 108 of the shaft 14d, along with the seal members 110 and 112, can be configured to slidably receive a guide wire or other intravascular device without the use of the guide lumen 44d. The elimination of the guide lumen would allow the shaft to be configured with a smaller outer diameter, thus reducing the profile of the catheter.

In operation of the intravascular apparatus 10, intravascular access is initially made in a conventional manner. If the procedure is a percutaneous translumenal angioplasty (PCTA) procedure, access is made via the femoral artery. A conventional introducer and guiding catheter (not shown) can be employed in a manner that is well known in the art. When used with the described embodiments of the present invention, a guiding catheter should have a lumen of sufficient size to accommodate the catheter 12, guide lumen 44 and guide wire 54.

To initially position the intravascular apparatus 10 in a patient's vessel, the guide wire 54 is preferably inserted into the guide lumen 44 while the entire guide lumen is outside the body such that the distal tip portion 58 of the guide wire 54 extends beyond the guide lumen 44. The combination of the guide wire 54 and guide lumen 44 is then advanced to a desired location in a vessel, and the catheter 12 is advanced over the guide lumen 44. The guide wire 54 can be inserted into the vessel prior to advancement of the guide lumen 44 over the guide wire, or the guide lumen 44 can be inserted into the vessel prior to advancement of the guide wire 54 through the guide lumen 44. If the catheter 12 is configured to receive the guide wire 54 without the guide lumen 44, the guide wire 54 can be advanced to a desired location in a vessel in a "bare wire" technique and the catheter 12 can be passed over the guide wire 54.

Preferably, the combination guide wire 54 and guide lumen 44 are advanced until the distal portions 48 and 58 thereof reach a distal end of the guiding catheter. The guide wire 54 may be further advanced in the vessel alone, or the guide lumen 44 may be advanced along with the guide wire 54. Thus, the distal portion 48 of the guide lumen 44 can provide additional support for the distal portion 58 of the guide wire 54 when desired. For example, when the guide wire 54 is initially advanced alone, it may become difficult at some point to further advance the guide wire because it does not have sufficient stiffness for effective manipulation. The guide lumen 44 can then be advanced to support the guide wire 54 and assist its advancement in the vessel. Thus, using the guide lumen 44 may avoid having to exchange the guide wire 54 for another guide wire having a larger diameter. If an exchange is required because the size or configuration of the guide wire 54 is inappropriate for further advancement in the vessel, the guide lumen 44 is advanced until the distal end 53 reaches a distal end 60 of the guide wire 54. The guide wire 54 is withdrawn from the guide lumen 44, and a desired bend can be formed in the distal portion 58 of the guide wire 54 or another guide wire can be obtained. The newly configured guide wire is then advanced through the guide lumen 44 to the previously attained position.

The guide lumen 44 can also be used to straighten a bend in the distal portion 58 of the guide wire 54 while inside a vessel. As noted above, the distal portion 58 of the guide wire 54 is often bent a desired amount prior to insertion into the body of a patient to allow manipulation of the guide wire 54 through various vessels. The distal portion 58 of the guide wire 54 may also bend as a result of advancement of the guide wire 54 when movement of the distal tip is impeded in the vessel. If the bend is inappropriate for further advancement of the guide wire 54 to the desired location in the vessel or for advancement into a different vessel, the guide lumen 44 can be advanced over the guide wire 54 to straighten the distal portion 58 a desired amount. In addition, the guide lumen 44 can be advanced over the guide wire 54 after the guide wire is advanced past a stenosis in the vessel to pre-dilate the stenosis before insertion of the balloon 20. The guide wire 54 can also be moved within the guide lumen 44 when the balloon 20 is inflated inside a vessel.

As best shown in FIG. 1, a substantial portion of the guide lumen 44 and guide wire 54 is positioned outside the catheter shaft 14 to allow a single-operator exchange of the catheter 12 for a second catheter. When a different size or configuration catheter is required, the catheter 12 is withdrawn so that the balloon 20 passes over the guide lumen 44 while an operator maintains a hold on the proximal portion 46 of the guide lumen 44 and the proximal portion 56 of the guide wire 54. The balloon of a second catheter can then be advanced over the guide lumen 44 to position the second catheter in the same location previously attained by the first balloon catheter 12. This single-operator exchange type configuration allows the operator to maintain a hold on the guide lumen 44 and guide wire 54 without using an extension or a relatively long guide lumen and guide wire.

The guide lumen 44 therefore provides for the independent or substantially contemporaneous exchange of the guide wire 54 and the catheter 12. When an exchange of the guide wire 54 is required, the guide wire 54 is withdrawn through the guide lumen 44 and replaced with a second guide wire. Thus, the guide wire 54 can be exchanged before the catheter 12 has been inserted in the vessel, while the catheter 12 remains in the vessel, or after the catheter 12 has been withdrawn. Likewise, the catheter 12 can be exchanged while the guide wire 54 remains in the vessel or after the guide wire 54 has been withdrawn. In either procedure, the position of the guide lumen 44 is maintained in the vessel by holding onto the proximal portion 46 of the guide lumen.

Figure 20:
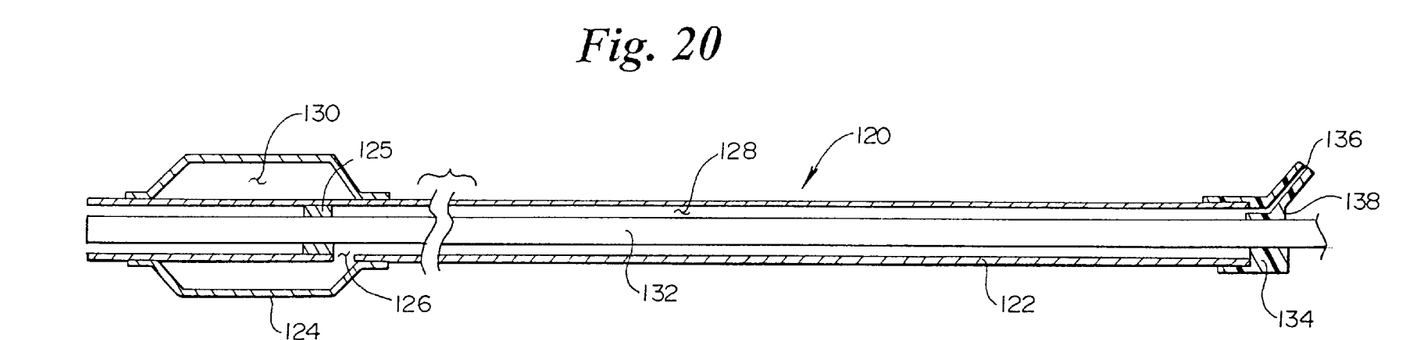
FIG. 20 is a side view, partially in section, of a sixth preferred embodiment of a balloon dilatation catheter.
Figure 21:
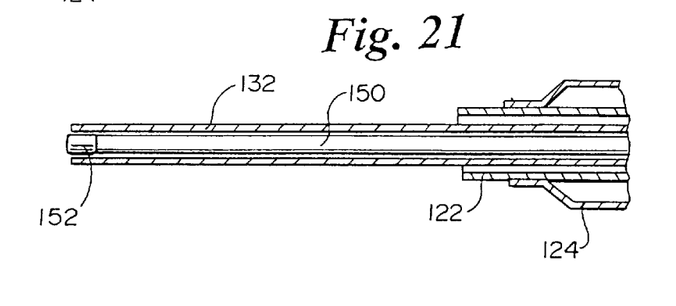
FIG. 21 is a side view, partially in section, of the embodiment shown in FIG. 20, with the guide member and IVUS device extended distally of the dilation balloon.

Referring now to FIGS. 20–21, an over-the-wire type balloon dilatation catheter is indicated generally at 120. In accordance with the illustrative embodiment, the balloon catheter 120 includes an inflation tube 122 with an inflation lumen 128 extending therethrough. Attached to a distal end portion of the inflation tube 122 is an inflatable balloon 124. The interior 130 of the inflatable balloon 124 is in fluid communication with the inflation lumen 128 of the inflation tube 122, via inflation port 126.

The proximal end of the inflation tube is attached to a proximal manifold 134. The proximal manifold 134 includes a fluid port 136, which is in fluid communication with the inflation lumen 128 as shown. The inflatable balloon 124 is expanded by applying fluid pressure to the inflation lumen 128 via fluid port 136.

To provide a longitudinally extending guide wire lumen, it is contemplated that an elongated guide member 132 may be provided. The elongated guide member 132 preferably coextends interiorly within at least a portion of the inflation lumen 128, and is in a slidable relation therewith. Because the elongated guide member 132 coextends interiorly within at least a portion of the inflation lumen 128, a seal 125 is provided. The seal 125 slidably receives the guide member 132 and provides a seal between the inflation lumen 128 and the exterior of the intravascular catheter 120.

In a preferred embodiment, the seal 125 comprises a seal between the inflation tube 122 and the guide member 132, as shown. The seal 125 may be a friction fit seal, such as an O-ring seal. In this configuration, the guide member 132 may be slidably positioned relative to the dilatation balloon 124. In addition, an IVUS device 152 which is positioned within the guide member 132, may be slidably positioned relative to the dilatation balloon 124 (see, FIG. 21). It is contemplated that a seal 138 may be provided between the manifold 134 and the guide member 132.

During an angioplasty procedure, the balloon 124 is positioned adjacent an occluded site within a vessel (not shown) and inflated to dilate the occluding matter. To view the revascularized portion of the vessel, the IVUS device 152 may be advanced down the guide member 132 until the IVUS device 152 is adjacent the desired site.

Figure 22:
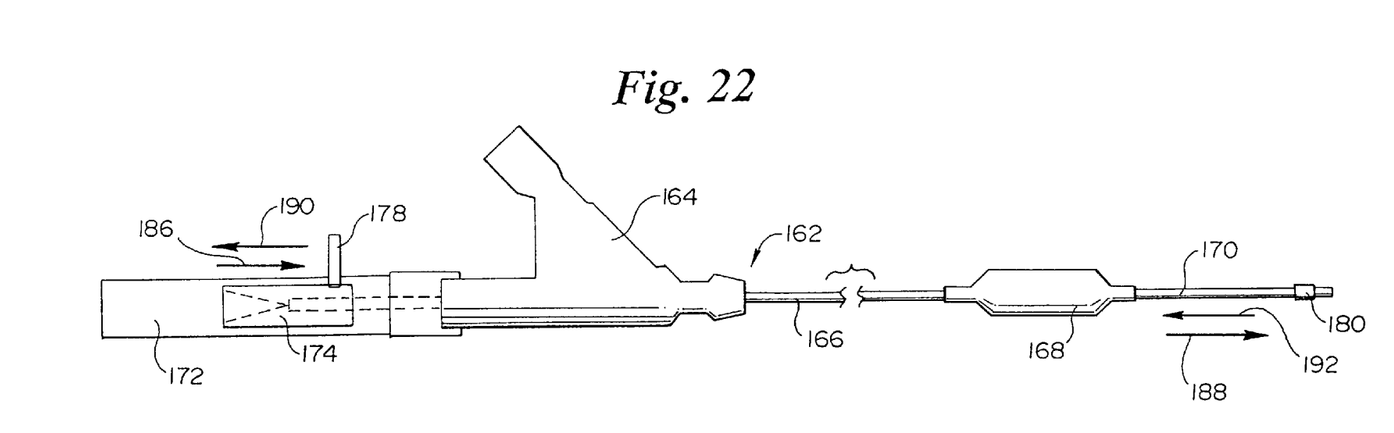
FIG. 22 is a side view, partially in section, of a lumen extension device coupled with a conventional over-the-wire balloon dilatation catheter.

Thereafter, the balloon dilatation catheter 120 may be withdrawn proximally relative to the guide member 132, as shown in FIG. 22. In this configuration, the dilatation balloon 124 is effectively moved proximally away from the IVUS device 152, and the IVUS device 152 and the guide member 132 remain adjacent the revascularized portion of the vessel. The IVUS device 152 may then be used to provide an image of the occluded vessel. Preferably, the IVUS device 132 remains within the guide member 132 so that the guide member 132 can provide protection to the IVUS device 152.

Because the guide member 132 remains across the occluded site or lesion, the balloon catheter 120 can easily be repositioned across the site by simply advancing the balloon catheter 120 over the guide member 132. This provides an efficient means for imaging a vessel between selected dilatations.

In accordance with the above, an illustrative method is contemplated that includes the steps of: providing a catheter 120 that has a movable guide member 132 therein and a balloon 124 located on the distal end thereof, wherein the catheter 120 is positioned within the body such that the balloon 124 is located adjacent a selected portion of the vessel; providing an elongated device 150 that has an imaging device 152 located near the distal end thereof, wherein the elongated device 150 is positioned within the guide member 132 as shown; moving the catheter 120 proximally of the selected portion of the vessel while leaving the movable guide member 132 substantially stationary relative to the selected portion of the vessel; positioning the imaging device 152 adjacent the selected portion of the vessel, if necessary; and imaging the selected portion of the vessel with the imaging device 152.

In an alternative method, it is recognized that the movable guide member may have a distal portion thereof positioned distal of the balloon by actually sliding the movable guide member in a distal direction while the balloon remains substantially stationary if it is desired to image distal of the balloon. Further, it is recognized that a combination of moving the balloon catheter and associated balloon in a proximal direction and moving the movable guide member in a distal direction can also be utilized. In either method or combination, the desired results is achieved in that the movable guide member has a distal portion thereof positioned distal of the balloon of the balloon catheter for use of an imaging device.

Figure 23:
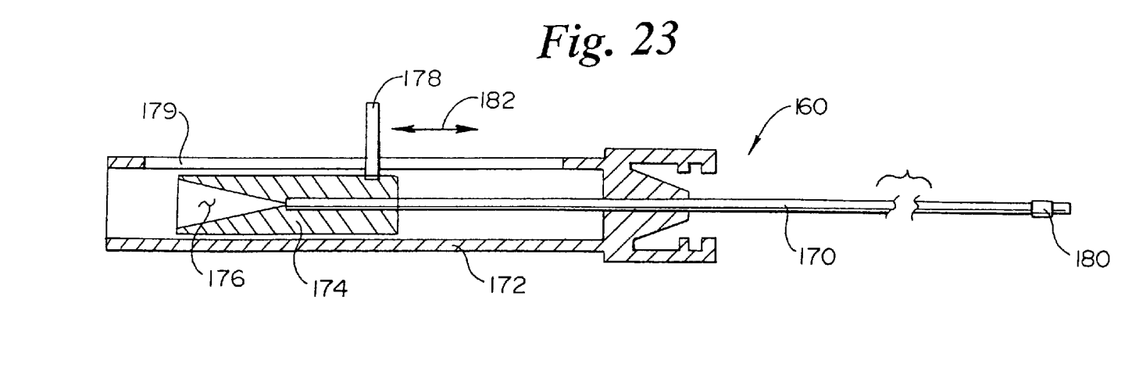
FIG. 23 is a side view, partially in section, of the lumen extension device shown in FIG. 22.

Referring now to FIGS. 22–23, a standard over-the-wire type balloon dilatation catheter is indicated generally at 162. In the illustrative embodiment, the standard balloon catheter 162 is combined with a lumen extension device 160 (see, FIG. 23). The lumen extension device 160 is a separate device that is used in conjunction with catheter 162. The lumen extension device 160 allows a user to effectively extend the guide wire lumen of a standard catheter 162 by a selected amount.

In the illustrative embodiment, the lumen extension device 160 includes an elongated guide member 170 for slidably receiving an elongated device, such as an IVUS device (not shown). The guide member 170 is adapted to be slidably disposed within the guide wire lumen of the standard catheter 162. Attached to the proximal end of the guide member 170 is a housing 172. The housing 172 preferably engages the proximal end of the catheter 162, and has a control mechanism 174 for controlling the relative longitudinal position of the guide member 170 relative to the catheter 162. Preferably, the catheter 162 has a manifold 164 on the proximal end thereof, and the housing 172 is attached to the manifold 164, as shown in FIG. 22.

The control mechanism 174 of the lumen extension device 160 preferably comprises a block that is slidably disposed in the housing 172. The block is attached to the proximal end of the guide member 170. Attached to the block is a handle 178, and the handle 178 extends out of the housing 172 through a slot 179. By manipulating the handle 178, the longitudinal position of the guide member 170 relative to the housing 172 may be changed, as shown at 182.

Since the housing 172 is preferably mounted to a manifold 164 of catheter 162, the handle 178 may be used to change the longitudinal position of the guide member 170 relative to the catheter 162. For example, by moving the handle proximally as shown at 190, the guide member 170 may be moved proximally relative to the balloon 168, as shown at 192. Likewise, by moving the handle distally, as shown at 186, the guide member 170 may be moved distally relative to the balloon 168, as shown at 188. Preferably, the block 174 has a tapered aperture 176 for guiding an elongated device, such as a IVUS device into the guide member 170.

In accordance with this embodiment, a method is contemplated including the steps of: providing a catheter 162 that has a guide wire lumen extending longitudinally therethrough, and a balloon 168 located on the distal end thereof, the catheter 162 being inserted into the body such that the balloon 168 is positioned adjacent a selected portion of a vessel (not shown); providing a lumen extension device 160 comprising a elongated tube 170, wherein the lumen extension device 160 is slidably positioned within the guide wire lumen of the catheter 162; providing an elongated device (not shown) that has an imaging device located near the distal end thereof, said elongated device being positioned within the elongated tube 170 of the lumen extension device 160; moving the catheter 162 proximally of the selected portion of the vessel while leaving the lumen extension device 162 substantially stationary relative to the selected portion of the vessel; positioning the elongated device (not shown) adjacent the selected portion of the vessel, if necessary; and imaging the selected portion of the vessel with the imaging device.

As with the other disclosed embodiments, an alternative method can include extending a distal portion of the elongated tube of the lumen extension device distal of the balloon while maintaining the balloon in a stationary position if it is desired to image distal of the balloon. Further, a combination of moving the elongated tube in a distal direction and the balloon in a proximal direction can also be utilized so that the elongated tube distal portion is positioned distal of the balloon.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the following claims, including all equivalents thereof, which are intended to define the scope of the invention.

What is claimed is:

1. An intravascular catheter, comprising:
   an elongated inflation tube with an inflation lumen extending therethrough;
   an inflatable balloon secured to a distal end portion of the inflation tube and in fluid flow communication with the inflation lumen;
   an elongated device;
   an elongated guide member adapted to slidably receive said elongated device, said guide member coextending interiorly within at least a portion of the inflation lumen and being selectively moveable relative to the inflation tube; and
   sealing means for slidably receiving the guide member and for providing a seal between the inflation lumen and the exterior of the intravascular catheter.

2. An intravascular catheter according to claim 1 wherein said elongated device is a guide wire.

3. An intravascular catheter according to claim 1 wherein said elongated device is an elongated member having an Intra-Vascular Ultra-Sound (IVUS) device located near the distal end thereof.

4. An intravascular catheter according to claim 1 wherein said sealing means comprises a seal between the inflation tube and the guide member.

5. An intravascular catheter according to claim 1 wherein the elongated guide member coextends interiorly within at least a distal portion of the inflation lumen.

6. An intravascular catheter, comprising:
   an elongated inflation tube with an inflation lumen extending therethrough;
   an inflatable balloon secured to a distal end portion of the inflation tube and in fluid flow communication with the inflation lumen, the inflatable balloon having a distal end;
   an elongated device;
   an elongated guide member adapted to slidably receive said elongated device, said guide member coextending interiorly within at least a portion of the inflation lumen and being selectively moveable relative to the inflation tube, said elongated guide member also capable of extending distal of the distal end of the inflatable balloon; and
   sealing means for slidably receiving the guide member and for providing a seal between the inflation lumen and the exterior of the intravascular catheter.

7. An intravascular catheter, comprising:
   an elongated inflation tube with an inflation lumen extending therethrough;
   an inflatable balloon secured to a distal end portion of the inflation tube and in fluid flow communication with the inflation lumen via an inflation opening in the inflation tube;
   an elongated device;
   an elongated guide member adapted to slidably receive said elongated device, said guide member coextending interiorly within at least a portion of the inflation tube and being selectively moveable relative to the inflation tube; and
   seal means positioned within the inflation lumen and adapted to slidably receive the guide member therethrough, said seal means providing a seal between the inflation lumen and the exterior of the intravascular catheter.

8. An intravascular catheter according to claim 7 wherein said sealing means comprises a seal between the inflation tube and the elongated guide member.

9. An intravascular catheter according to claim 8 wherein the seal is positioned distally of the inflation opening in the inflation tube.

10. An intravascular catheter according to claim 9 wherein the seal is a friction fit seal.

11. An intravascular catheter according to claim 10 wherein the seal is provided by at least one O-ring.

12. An intravascular catheter according to claim 7 wherein said elongated device is a guide wire.

13. An intravascular catheter according to claim 7 wherein said elongated device is an elongated member having an Intra-Vascular Ultra-Sound (IVUS) device located near the distal end thereof.

14. An intravascular catheter according to claim 7 wherein the elongated guide member coextends interiorly within at least a distal portion of the inflation lumen.

* * * * *